US00PP35175P2

(12) United States Plant Patent
Hansen

(10) Patent No.: US PP35,175 P2
(45) Date of Patent: May 16, 2023

(54) ***HOSTA* PLANT NAMED 'DANCING IN THE MOONLIGHT'**

(50) Latin Name: ***Hosta* hybrid (Tratt.)**
Varietal Denomination: Dancing in the Moonlight

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,735

(22) Filed: Nov. 1, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02
See application file for complete search history.

*Primary Examiner* — Kent L Bell

(57) ABSTRACT

A new and distinct *Hosta* plant named 'Dancing in the Moonlight' producing medium-sized upright mounds of basal, lanceolate leaves with long, narrowly acute apices, cordate bases and intensely wavy margins and strongly folded along the midrib. The leaves are variegated having medium green centers and creamy-white margins with intermediate color separation between the margin and center of variably large segments of several shades of chartreuse. The medium-sized leaves have a matte and lightly glaucous upper surface and heavily glaucous underside. The campanulate flowers are very pale lavender beginning in mid-July. Each flower is attractively subtended by a floral bract with purplish margin making the scape showy for long periods. 'Dancing in the Moonlight' is useful in the landscape, as a container plant, a specimen or en masse.

2 Drawing Sheets

Botanical classification: *Hosta* hybrid (Tratt.).
Variety denomination: 'Dancing in the Moonlight'.

STATEMENT REGARDING PRIOR DISCLOSURES UNDER 37 CFR 1.77(B)(6)

*Hosta* 'Dancing in the Moonlight' was first introduced by the inventor as a non-enabling description in registration of the name in early 2021 with the International Cultivar Registration Authority for the genus *Hosta*. No plants of *Hosta* 'Dancing in the Moonlight' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Dancing in the Moonlight' hereinafter also referred to as the new plant or by the cultivar name, 'Dancing in the Moonlight'. *Hosta* 'Dancing in the Moonlight' was hybridized by the inventor on Jul. 14, 2015, at a wholesale perennial nursery in Zeeland, Mich., USA. The female parent was the proprietary unreleased hybrid known only by the hybrid number H10-132 (not patented) and the male parent was the proprietary unreleased hybrid known only by the hybrid number H10-366 (not patented). The seeds from this cross were planted in late fall of 2015 and a single seedling selection from this cross eventually was selected as the new plant. The new plant was assigned the breeder code 12-132-4 and passed the initial evaluation in the summer of 2018. 'Dancing in the Moonlight' has been asexually propagated by division at the same nursery since 2018 and also by careful shoot tip plant tissue culture with the resultant asexually propagated plants having retained all the same traits as the original plant. *Hosta* 'Dancing in the Moonlight' has been stable and reproduced true to type plants in successive generations of asexual reproduction.

There are over 7,000 registered and established *Hosta* cultivars with The American Hosta Society, which is the International Cultivar Registration Authority for the genus *Hosta*. Several of these have blue-green leaf blades. The most similar *Hosta* cultivars known to the applicant are: 'Minnesota Wild' (not patented), 'High Diver' (not patented), 'Barracuda' (not patented), and 'Summer Wind' (not patented).

The female parent is much smaller with green foliage that was irregularly streaked with creamy white. The male parent has solid bluish-green, rippled, and arching foliage.

'Minnesota Wild' has a more rounded less upright habit, the leaves are broader with less acute apices, more consistent and wider margins, less folded, and less sinuate. 'High Diver' has leaves that are less sinuate and less folded. 'Barracuda' is smaller and more arching in habit with a more lustrous, less sinuate and less folded leaves. 'Summer Wind' has more arching habit, the foliage that is less sinuate, and less folded-green.

Other *Hosta* cultivars may have individual traits similar to 'Dancing in the Moonlight' but the new plant differs from the above listed cultivars and all other *Hostas* known to the applicant, by the combination of the following traits.

1. Leaves are medium-sized, lanceolate, with long, narrowly, acute apices and cordate bases;
2. Leaves are furrowed with an intensely wavy margin with twisted leaf apices;
3. Leaf margins are creamy white, the mature center color is medium green with intermediate color separation between the margin and center;

4. Campanulate flowers are very pale lavender on upright, light-green, moderately glaucous scapes beginning in mid-July;
5. Flowers are moderately loosely arranged on scapes with the first flowers beginning to open well above the foliage;
6. Floral bracts with a purplish margin subtend each flower;
7. The habit is a medium-sized upright mound.

BRIEF DESCRIPTION OF THE DRAWING

The photograph of the new plant demonstrates the overall appearance of the new plant, including the unique traits. The colors are as accurate as reasonably possible with color reproductions. Ambient light spectrum, temperature, source and direction may cause the appearance of minor variation in color.

The drawings show a ten-year-old 'Dancing in the Moonlight' plant in a trial garden at a nursery in Zeeland, Mich. with supplement fertilizer and water as needed.

DETAILED BOTANICAL DESCRIPTION

Figure 1:
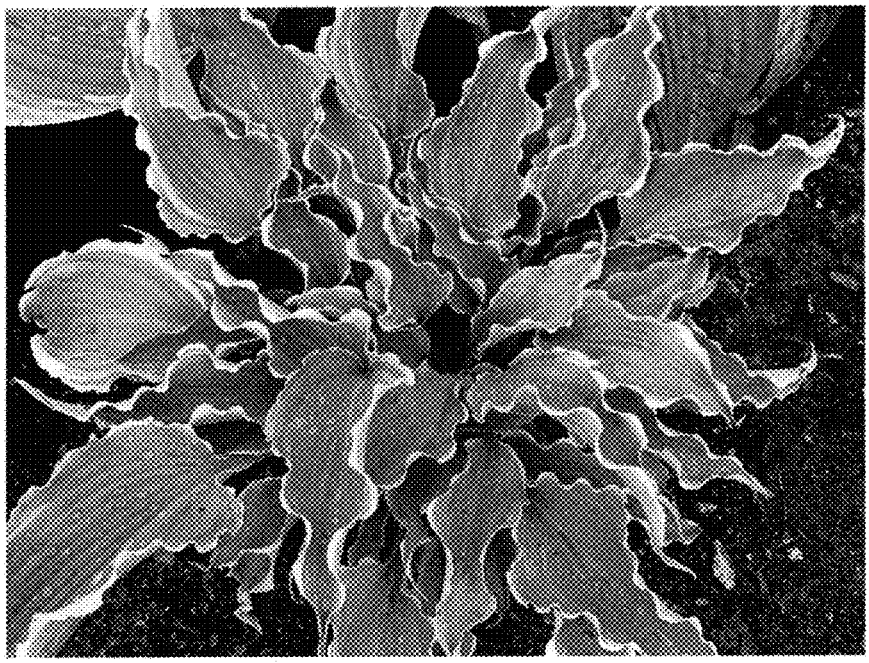
FIG. 1 shows the landscape foliage habit of a new plant prior to flowering.
Figure 2:
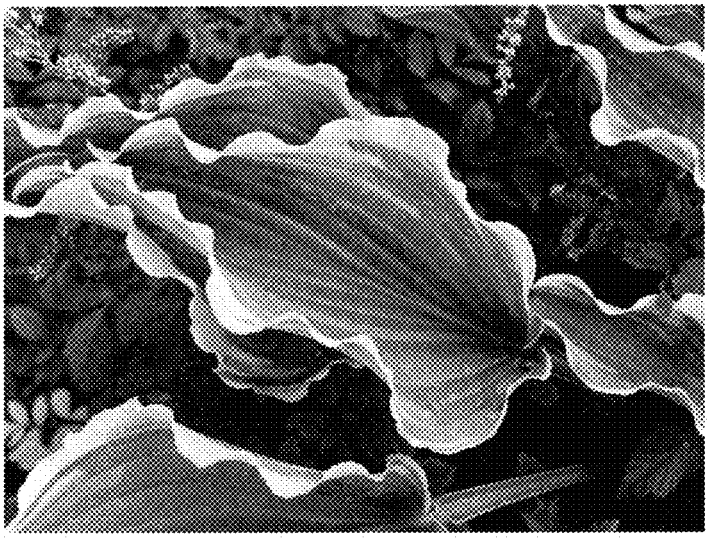
FIG. 2 shows a close-up of a leaf.
Figure 3:
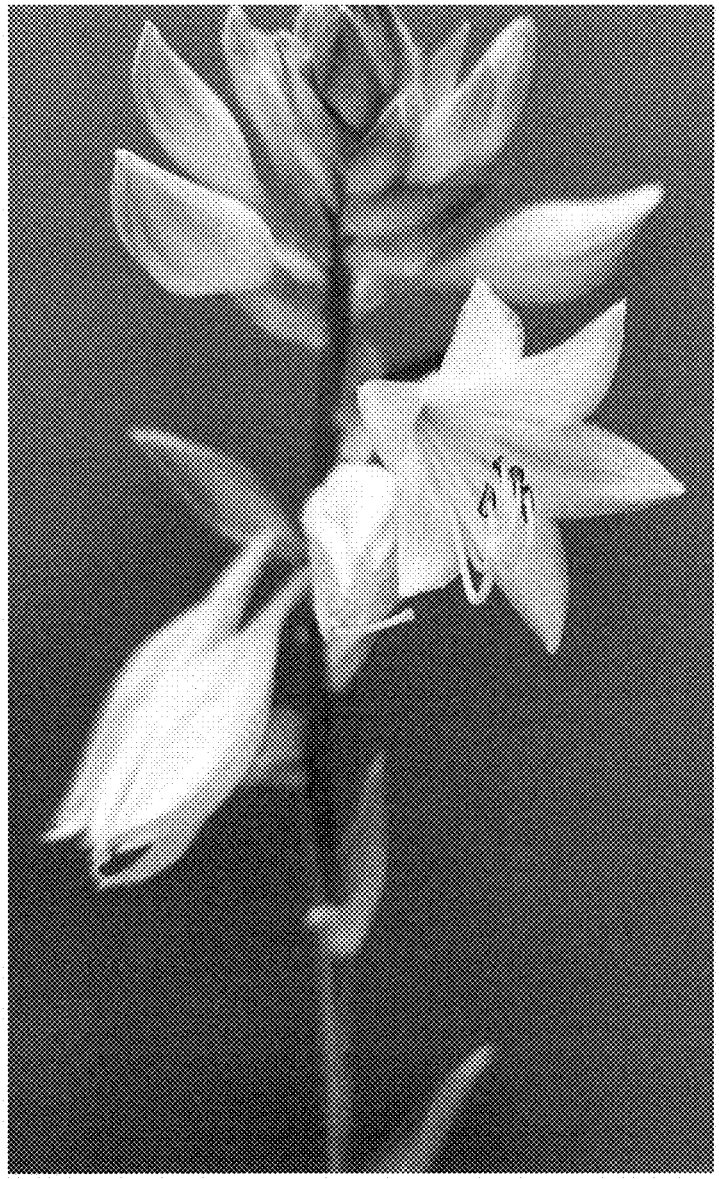
FIG. 3 shows a close-up of the flower, buds and foliar bracts.

The following descriptions and color references are based on the 2015 edition of The Royal Horticultural Society Colour Chart except where common dictionary terms are used. The new plant, *Hosta* 'Dancing in the Moonlight', has not been observed under all possible environments. Those skilled in the art will appreciate that certain characteristics will vary in plants that are more mature or plants that are less mature. The phenotype may vary slightly with different environmental conditions, such as temperature, light, fertility, moisture and maturity levels, but without any change in the genotype. The following observations and size descriptions are of a ten-year-old plant in a shaded trial garden in Zeeland, Mich. with supplemental water and fertilizer.

Botanical classification: *Hosta* x hybrid;

Parentage: Female or seed parent is a proprietary hybrid H10-132; male or pollen parent is the proprietary hybrid H10-336; the complex hybrid comprises 'Neptune' U.S. Plant Pat. No. 19,674, 'Medusa' (not patented), 'Joy Ride' (not patented), 'Niagara Falls' (not patented), 'Fulda' (not patented), and a selection from *H. venusta* (not patented).

Propagation: Garden division and sterile shoot tip tissue culture;

Time to initiate roots from tissue culture: About three weeks;

Growth rate: Moderately vigorous to slow;

Crop time: About four months to six months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing an upright medium-sized mound of leaves and erect scapes, arching toward ends, flowering above foliage;

Plant size: Foliage height to about 45 cm above soil line to the top of the leaves, to about 60 cm tall to the top of the flowers and to about 74 cm wide at the widest point about 25 cm above the soil line;

Foliage description: Lanceolate; furrowed or folded along midrib; long, narrowly-acute, bent or twisted apex; cordate base; margin entire, and intensely sinuate; not bullate between the veins, glabrous and smooth both surfaces; adaxial lightly glaucous and abaxial strongly glaucous; flexible; variegated with medium green center and creamy-white margins; margin width variable, between 3 mm and 13 mm;

Leaf blade size: To about 26 cm long and about 13 cm wide about one-third of the way from base; average about 23.5 cm long and 11.5 cm wide;

Leaf blade color: Early season and expanding adaxial margin nearest RHS 146D, center between RHS 146B and RHS 150D with intermediate zone comprising colors of nearest RHS 146D, between RHS N144A and RHS N144D, and between RHS 147C and RHS 145C; mid-season and mature adaxial margin nearest RHS 4D in more light intensity and nearest RHS 4B with heavy shade, center between RHS 137A and RHS 137B with light glaucous coating, with intermediate zone comprising colors of between RHS 191B and RHS 191C, nearest RHS 146D, and nearest RHS N138B; abaxial early season and expanding leaf margin nearest RHS 4D, center between RHS 1378 and RHS 137C, with intermediate zone comprising colors of nearest RHS N138B, between RHS 189C and RHS N138C, and nearest RH5 139D; abaxial mid-season and mature margin nearest RHS 4D, center between RHS 138A and RHS 138B with heavy glaucous coating producing color between RHS 191B and RHS 190A, with intermediate zone comprising colors of between RHS 146D and RHS 145C, and nearest RHS 190C;

Veins: 8 to 10 pairs with midrib; slightly impressed adaxial and costate and slightly asperous abaxial;

Vein color: Young adaxial nearest RHS 146D, young abaxial nearest RHS 146D proximally maculate with nearest RHS N186C; mature adaxial margin nearest RHS 156B and center nearest RHS 138B, mature abaxial margin between RHS 158D and RHS 156C, center nearest RHS 146D;

Petiole: Glabrous, lightly glaucous, and matte both adaxial and abaxial; moderately concavo-convex; stiff; to 30 cm long and 18 mm wide and about 10 mm deep at base, average about 25 cm long and 14 mm wide and 7 mm deep;

Petiole color: Distal portion adaxial margin nearest RHS 4D, center between RHS 146D and RHS 145A; proximal adaxial portion margin between RHS 147C and RHS 147D, center nearest RHS 146D with more concentrated maculate proximally with larger longitudinal spots to 3 mm long and 1 mm across of nearest RHS N186C; abaxial distal margin nearest RHS 4D, midrib nearest RHS 145C and region between margin and midrib nearest RHS 138A; abaxial proximal margin and center including midrib between RHS 145B and RHS 145C with more concentrated maculate proximally with larger longitudinal spots to 3 mm long and 1 mm across of nearest RHS N186C;

Flower description:

Buds one to two days prior to opening: Clavate with acute apex and narrow tube and rounded base; about 45 mm long and 12 mm in diameter at the widest portion in the bulb, tube to about 16 mm long and to about 3 mm diameter at base, gradually tapering from bulb; bulb about 29 mm long;

Bud color: Near white in the center a blend of RHS NN155C and RHS 85D, with apical 6 mm variable nearest RHS 85C and RHS 85D, basal tube nearest RHS 85D;

Flowers: Perfect; incomplete; campanulate; attitude outwardly to slightly downwardly; to 60 mm long to exserted pistil; corolla to 55 mm long and 38 mm wide at apex, fused in basal 35 mm, free in the distal 20 mm, decreasing in size distally; corolla tube portion 18 mm long and gradually tapering to 3 mm diameter at base; with rounded base; flowers moderately loosely arranged on scape;

Flower aspect: Outwardly;

Flowering lasting: Persists for a normal period, usually about one day on the plant;

Flowering period: Scapes remain effective with flowers beginning mid-July for about three weeks; with about 30 flowers per scape; mostly secund;

Fragrance: No detectable fragrance;

Tepals: Two sets of three; lanceolate; entire margins; acute apex; fused in basal 35 mm; glabrous adaxial and abaxial; outer set reflexed, to about 11 mm wide near fusion and 55 mm long; inner set to about 10 mm wide and 55 mm long;

Tepal color: Outer set adaxial nearest RHS 85D in 2.5 mm wide longitudinal center and nearest RHS NN155D along edges, abaxial lighter than RHS 85D in flared portion and nearest RHS NN155D along edge; inner set adaxial nearest RHS 85D in 6 mm wide longitudinal center and nearest RHS NN155D along edges, abaxial lighter than RHS 85D in flared portion and nearest RHS NN155D along edge, with a transparent 0.5 mm wide margin; corolla tube adaxial nearest RHS NN155C, abaxial nearest RHS 85D;

Gynoecium: Single; to about 64 mm long; superior;

*Style*.—Cylindrical; glabrous; to about 58 mm long and 0.7 mm diameter; straight with distal 10 mm arcuate upwards 90°; color nearest RHS NN155A.

*Stigma*.—Puberulent; tri-lobed; about 1 mm long and 1 mm diameter; color nearest RHS NN155A.

*Ovary*.—Ellipsoidal; superior; apex rounded; base rounded to truncate; sides slightly furrowed, about 5 mm long and 2.5 mm diameter; color nearest RHS 145C.

Androecium: Six;

*Filaments*.—Six; cylindrical; approximately 57 mm long and 0.5 mm in diameter; curved or bent upwardly about 90° in the distal 8 mm; color nearest RHS NN155A.

*Anthers*.—Oblong with rounded ends; basifixed, longitudinally dehiscent; about 5 mm long and 2 mm wide and 1.5 mm thick when fully developed; color adaxial between RHS 65B and RHS 65C, abaxial nearest RHS 162C.

*Pollen*.—Abundant; spherical; less than 0.1 mm long; color nearest RHS 17A.

Peduncle: Cylindrical; usually one per mature division; about 5 per plant; glabrous; moderately glaucous; erect to slightly drooping distally; to about 65 cm tall, and about 9 mm in diameter at base, average about 60 cm tall and 5 mm diameter at base;

Peduncle color: Between RHS 148C and RHS 138B without noticeable anthocyanin blush pigmentation;

Inflorescence: Flowering portion about 28 cm long and 7.5 cm wide; with faintly variegated bracts subtending each flower;

Pedicel: Cylindrical; glabrous; slightly lustrous; to about 20 mm long and 2.0 mm diameter, decreasing distally; attitude arcuate outwardly;

Pedicel color: Nearest RHS 148D proximally and RHS 157D distally without significant anthocyanin;

Floral bracts: Each flower normally subtended by a single faintly variegated bract; lanceolate; narrowly acute apex and truncate base; entire margin; glabrous and slightly glaucous abaxial and adaxial; to about 38 mm long 14 mm wide, decreasing distally; variegated margin about 1 mm wide;

Bract color: Proximal bracts at flowering adaxial and abaxial margin nearest RHS NN155B, adaxial and abaxial center between RHS 145A and RHS 146D; distal bracts at flowering adaxial margin between RHS N75D and RHS N77C, abaxial margin nearest RHS N77C, adaxial center nearest 145D and abaxial center between RHS 145D and RHS 146D;

Fruit: Non-fleshy, dehiscent, tri-loculicidal capsule; oblong ellipsoidal; rounded base; acute to apiculate apex; about 16 mm long and 5 mm in diameter; color as maturing nearest RHS 146D, when nearly mature and prior to dehiscence nearest RHS 158A and upon dehiscence nearest RHS 161C;

Seeds: Elliptic; with flattened wing surrounding embryo positioned toward one end of ellipse; about 7 mm long, 2 mm wide and 1 mm thick at embryo; typically 12 to 18 per capsule; color nearest RHS 202A with maturity;

Disease and pest resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth: The plant grows best and shows best coloration with plenty of moisture, adequate drainage and light shade, but is able to tolerate some drought when mature.

Hardiness: At least from USDA zone 3 through 8.

It is claimed:

1. A new and distinct *Hosta* plant named 'Dancing in the Moonlight' as herein described and illustrated.

* * * * *